(12) United States Patent
Jacobsen et al.

(10) Patent No.: US 6,198,394 B1
(45) Date of Patent: Mar. 6, 2001

(54) SYSTEM FOR REMOTE MONITORING OF PERSONNEL

(76) Inventors: Stephen C. Jacobsen; Roland Wyatt; Stephen C. Peterson; Tomasz J. Petelenz, all of 360 Wakara Way, Salt Lake City, UT (US) 84108

( * ) Notice: Subject to any disclaimer, the term of this patent is extended or adjusted under 35 U.S.C. 154(b) by 0 days.

(21) Appl. No.: 08/760,855

(22) Filed: Dec. 5, 1996

(51) Int. Cl.⁷ .................................................. G08B 25/10
(52) U.S. Cl. ................. 340/573.1; 340/539; 340/825.15; 340/825.36; 340/825.54; 364/551.01
(58) Field of Search .................................... 340/573, 539, 340/825.06, 825.15, 825.36, 825.49, 825.54, 573.1; 364/551.01

(56) References Cited

U.S. PATENT DOCUMENTS

| | | | |
|---|---|---|---|
| 3,572,316 | * 3/1971 | Vogelman et al. | 180/437 |
| 3,646,606 | * 2/1972 | Buxton et al. | 600/483 |
| 3,846,704 | * 11/1974 | Bessette | 340/870.28 |
| 3,972,320 | * 8/1976 | Kalman | 600/519 |
| 4,129,125 | * 12/1978 | Lester et al. | 600/484 |
| 4,270,547 | 6/1981 | Steffen et al. | 600/484 |
| 4,312,358 | * 1/1982 | Barney | 128/670 |
| 4,331,154 | * 5/1982 | Broadwater et al. | 128/677 |
| 4,494,553 | * 1/1985 | Sciarra et al. | 128/721 |
| 4,531,527 | 7/1985 | Reinhold, Jr. et al. | 600/509 |
| 4,608,994 | * 9/1986 | Ozawa et al. | 128/670 |
| 4,867,170 | * 9/1989 | Takahashi | 128/677 |
| 4,867,442 | * 9/1989 | Matthews | 482/8 |
| 4,909,260 | * 3/1990 | Salem et al. | 128/721 |
| 4,966,154 | * 10/1990 | Cooper et al. | 128/671 |
| 5,022,402 | * 6/1991 | Schieberl et al. | 128/671 |
| 5,027,824 | 7/1991 | Dougherty et al. | 600/515 |
| 5,148,002 | 9/1992 | Kuo et al. | 219/211 |
| 5,153,584 | * 10/1992 | Engira | 340/573 |
| 5,204,670 | * 4/1993 | Stinton | 340/825.54 |
| 5,228,449 | * 7/1993 | Christ et al. | 128/691 |
| 5,263,491 | * 11/1993 | Thornton | 128/774 |
| 5,335,664 | * 8/1994 | Nagashima | 128/696 |
| 5,416,468 | * 5/1995 | Baumann | 340/573 |
| 5,515,858 | 5/1996 | Myllymäki | 600/301 |
| 5,544,651 | 8/1996 | Wilk | 600/310 |
| 5,724,025 | * 3/1998 | Tavori | 340/573.1 |
| 5,771,001 | * 6/1998 | Cobb | 340/539 |
| 5,778,882 | 7/1998 | Raymond et al. | 600/513 |

* cited by examiner

*Primary Examiner*—Glen Swann
(74) *Attorney, Agent, or Firm*—Thorpe, North & Western

(57) ABSTRACT

A system for remotely monitoring personnel status includes a plurality of sensors disposable on a soldier or other person for developing signals which may be used to determine the physiologicalal status. The sensors communicate with a soldier unit which can process the information to ensure that the sensor data falls within acceptable ranges and communicate with remote monitors. The soldier unit also includes a global positioning system. By using the sensor data and the global positioning system, leaders and medics can quickly and accurately track and treat casualties in battle. The system enables more rapid location of the casualty, as well as remote triage/initial diagnosis, thereby assuring that those who are most in need of treatment are attended to first. Typically, the system monitors both body surface and ambient temperature, heart rate, shivering, motion status and body condition. Additional sensors can be provided to supply information on other physiologicalal parameter which may be desired for more thorough diagnosis. The physiologicalal information may be stored and kept with the soldier to enable improved care as the soldier is moved to higher levels of care.

91 Claims, 11 Drawing Sheets

SYSTEM FOR REMOTE MONITORING OF PERSONNEL

BACKGROUND OF THE INVENTION

The present invention relates to a system for remote monitoring of personnel, and especially to a system for monitoring the well-being of military personnel on the battlefield and during training exercises. As will be apparent from the accompanying specification, the military version of the device can easily be modified for use in civilian medical care and medical monitoring of personnel working under adverse environmental conditions, such as firefighters, seamen, field maintenance personnel, etc.

During battle there are numerous causes of mortality, both direct and indirect, which, if avoided, would spare many lives. These include, but are not limited to:

1) fratricide (deaths from friendly fire);
2) deaths resulting from extreme environmental conditions;
3) deaths of medics and others during attempts to rescue those who are already dead or who are mortally wounded;
4) delay in locating casualties beyond the short period during which treatment most likely will be effective;
5) inadequate data to guide optimum initial evaluation by medical personnel in the field;
6) difficulty interpreting the available data in the stress of battle;
7) difficulty in maintaining consistent reevaluation during transport to and through higher levels of care; and
8) difficulty during peacetime in acquiring and maintaining combat trauma treatment skills by medical personnel.

It is believed that if some or all of these problems were adequately addressed, a considerable number of lives could be saved during combat situations. By providing accurate information about location and the physiological status of each individual, as well as communications equipment to convey the information to remote locations, a system for monitoring personnel could save many lives. During peacetime, monitoring physiological variables and location could be beneficial for people exposed to hazardous occupational and/or environmental conditions, such as law enforcement, firefighters, sailors, mountaineers and the like. Furthermore, such monitors could be extremely valuable for military and law enforcement personnel, such as the special forces, e.g. Rangers, who commonly train under extreme weather conditions, and in other dangerous environments. By monitoring physiological variables, those overseeing exercises can monitor the soldier, etc., and withdraw him/her from the exercise if it appears that harm is likely.

Currently, there are monitors which are used in athletic training and in hospitals so as to enable trainers or medical personnel to monitor the vital signs of an athlete or a hospital patient. See e.g. U.S. Pat. Nos. 5,022,402; 4909,260; 4,494,553; 4,129,125; and 3,572,316. Typically, these monitors are placed in wrist bands or belts which may be quickly attached to and removed from the athlete or patient. However, these monitors are generally insufficient for use in combat situations. For example, such monitors typically monitor a single vital sign, such as heart rate, or temperature. A few may monitor combinations of vital signs with limited accuracy or averaged over long periods of time. While this information is of some use for athletes, etc., it is insufficient for accurate determination of patients or casualties in need of immediate medical care or evaluation, and those who do not need or will not benefit from immediate care.

The monitors which are currently available also generally do not provide location information, let alone location information which is sufficiently accurate to quickly locate an injured person. By providing accurate information about the location of combat troops, a system for monitoring personnel prevents casualties due to friendly fire, i.e. combat forces accidentally injured by their colleagues, and enables medical staff to quickly locate and treat casualties.

Yet another problem with the presently available monitors is that they generally offer little, if any, diagnostic assistance. Rather than indicating that a particular physiological state has been reached, the presently available monitors typically only provide information about heart rate or other vital signs and leave all diagnoses and medical decisions to medical personnel who may be unavailable or delayed.

Still other problems with the presently available monitors are that they are not configured to withstand the rigors of military and other rugged environments; their communications configurations are not capable of integrating numerous different personnel within the system; and they do not readily adapt to frequent changes in the number of persons which are monitored by the system.

Thus there is a need for a monitoring system which may be worn by both military and nonmilitary personnel to monitor their vital signs and independently determine when certain physiological conditions are present which require either corrective non-medical action, such as withdrawal from extreme environments, and/or medical treatment. Such a system would preferably also provide a storage system for creating a medical record and enabling a continuous review of treatment as the injured person is passed to different levels of medical care. Such a system would further provide geolocation information so as to help prevent casualties from friendly fire, and to assist in location of casualties by medical personnel. In a civilian system, the geolocation information could be used to track the location of firefighters, seaman, and law enforcement officials.

The system may also include a means for transmitting, interpreting and displaying data at various locations. The monitoring system would thus comprise functional units deployed at different operational levels individual units (e.g. soldier status units); leader/medic units; and command units. All of the units are interconnected via the communication system, via a network, individually, or in any other combination.

SUMMARY OF THE INVENTION

It is an object of the present invention to provide a system for monitoring personnel which measures selected physiological variables and geolocation of a person during physical exercise/motion, stores and interprets this information, and communicates with higher echelons of command and medical care.

It is another object of the present invention to provide such a system for monitoring personnel which is inexpensive and easy to operate.

It is another object of the invention to provide a system for monitoring personnel which will not interfere with other communications equipment of the user.

It is an additional object of the invention to provide a system for monitoring personnel which will not be interfered with by radio frequency communications, and electromagnetic noise.

It is yet another object of the present invention to provide a system for monitoring personnel which is ergonomically designed so it will not interfere or will minimally interfere with the ability of soldiers or other personnel in the performance of their tasks and duties.

It is yet another object of the invention to provide a system for monitoring personnel which can be attached to a soldier to provide relatively continuous geolocation and physiological information about the soldier/user.

It is still another object of the present invention to provide such a monitoring system which will identify those who will and will not benefit from immediate treatment.

It is yet an additional object of the present invention to provide such a monitoring system capable of providing a history of physiological information about the soldier to which it is attached for subsequent retrieval, interpretation and, if necessary, medical treatment.

Still an additional object of the present invention is to provide such a monitoring system capable of developing data and feedback to assist in or regulate the administration of fluids, medications, and other therapies, e.g. ventilation.

The above and other objects of the invention are realized in specific illustrative embodiments of a system for monitoring personnel which include a plurality of sensors for developing signals which may be used to determine the physiological status of military and/or non-military personnel, the sensors being typically disposed in an integrated sensor unit. Typically, the integrated sensor unit may contain sensors to determine both skin surface and ambient temperature, heart rate, shivering, motion status and body position. Additional sensors can be provided in the integrated sensor unit or in a separate platform to supply information on other physiological factors such as oxygen saturation, blood pressure or breathing rate which may be desired to provide a more thorough diagnosis of an individual.

The information collected by the integrated sensor unit or other platforms is then forwarded to a personnel unit, hereinafter referred to as a soldier unit. Either the integrated sensor unit or the soldier unit includes a microprocessor and software/firmware which allow the soldier unit to monitor the physiological state of the user. The soldier unit also includes a communications system for transmitting signals representative of the physiological status obtained from the integrated sensor unit and geolocation to a leader/medic unit and/or a command unit at a remote location(s). The soldier unit may also contain a display and a means of sending an alert signal by a person wearing the unit, such as an alert button. The display can be located at any convenient location on the body, such as the wrist, head, arm, etc., and or be detachable from the soldier unit.

Once the information received from the integrated sensor unit has been processed, it is sent by the soldier unit to a remote leader/medic unit and/or a remote command unit. With the physiological information, the communications module also transmits information which enables geolocation of the military personnel.

The soldier unit will also typically include software/firmware for determining certain physiological states which are common in battlefield conditions, or which are particular to the field of use (firefighting, etc.) of the unit. When one or more of the critical limits are reached, the soldier unit sends a warning signal to the leader/medic unit and/or the command unit, thereby indicating that a soldier is in need of immediate care. For example, if the temperature sensors of the integrated sensor unit indicate cold weather and that the soldier's body temperature has begun to fall below a specified minimum, the soldier status unit will automatically signal the leader/medic unit and the command unit that the soldier is likely suffering from hypothermia. The leader or medic operating the leader/medic unit or a person operating the central control unit may then notify other soldiers or medical personnel in the area that the soldier should be treated for the condition as soon as possible. Similarly, a wounded soldier can be monitored for symptoms and severity of injury or shock ensuing from blood loss.

In accordance with one aspect of the invention, each soldier unit is customized to the particular wearer. Thus, the soldier unit may contain information about the individual such as allergies to medications and other medical information which would be important to medical personnel treating the individual. Additionally, the soldier unit may typically keep a short physiological history, such as the body temperature, heart rate, body positions, blood pressure, oxygen saturation and movement for the last four hours or some other time period. The information can be forwarded to a field leader/medic unit or the command unit upon request. This can be accomplished either by the remote communications system of the soldier unit, or by a direct link-up between the soldier unit and the leader/medic unit when a medic, et cetera, having a leader/medic unit, arrives to treat the user.

In accordance with another aspect of the invention, the soldier unit or leader/medic unit could include software/firmware for providing guidance and medical decision support. Additionally, a microprocessor disposed therein, or in the soldier unit, could be programmed to control fluid infusion, drug delivery, and ventilator support for the patient, thereby enabling efficacious treatment even under battlefield conditions.

In accordance with still another aspect of the invention, the soldier unit communicates with the leader/medic unit or command unit either continuously or in brief bursts so as to prevent enemy combat forces from tracking the communications to locate the soldier. The bursts may occur periodically on schedule, or as indicated by the leader/medic control unit or command unit.

In accordance with a further aspect of the invention, the leader/medic unit is a portable device worn by medics and other leaders to allow each to monitor those for whom they are responsible. The leader/medic unit contains a communications system for communicating with the soldier status units and the command units, and contains a display which allows the user to graphically monitor the locations of personnel on the battlefield, and/or to view the physiological conditions of each soldier within the command structure for that leader. The leader/medic unit receives information as to the location of the injured soldier, and receives medical information while the medic is relocating to the site of the soldier. When used by a medic, this unit enables the medic to view vital signs and other information about the injured soldier prior to actually examining the soldier. Thus, the medic is able to conduct an initial evaluation of the injured soldier while in transit to the soldier's location. Additionally, because the soldier unit also communicates with the command unit, medical personnel at a central command post can instruct the medic on diagnosis and treatment options as the medic is en route to the casualty.

The command unit comprises a command post base unit which is typically integrated with a portable computer. The command unit is able to view the locations of large groups of soldiers to prevent fratricide situations. The command unit also enables the monitoring of any individual soldier and provides a more comprehensive physiological condition history to improve subsequent treatment.

By continually monitoring the location and status of the soldiers, significant decreases in casualty rates can be achieved. Additionally, the technology used in the present invention can be modified slightly to maintain high levels of care in civilian medical applications while significantly decreasing the costs.

In addition, all units may be equipped with a removable, nonvolatile memory module which contains relevant personal records and acquired data. The soldier units could include means to remove/exchange the memory modules, whereas other units of the system for monitoring personnel have appropriate provisions for retrieving information from the memory modules. The memory modules, the attachment means and the sensors are sufficiently rugged for the operational environment. Thus, for example, a card having a magnetic strip for storing information may be used to download needed information. Likewise, a bar code reader may also be included for rapid entry of pre-coded information.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
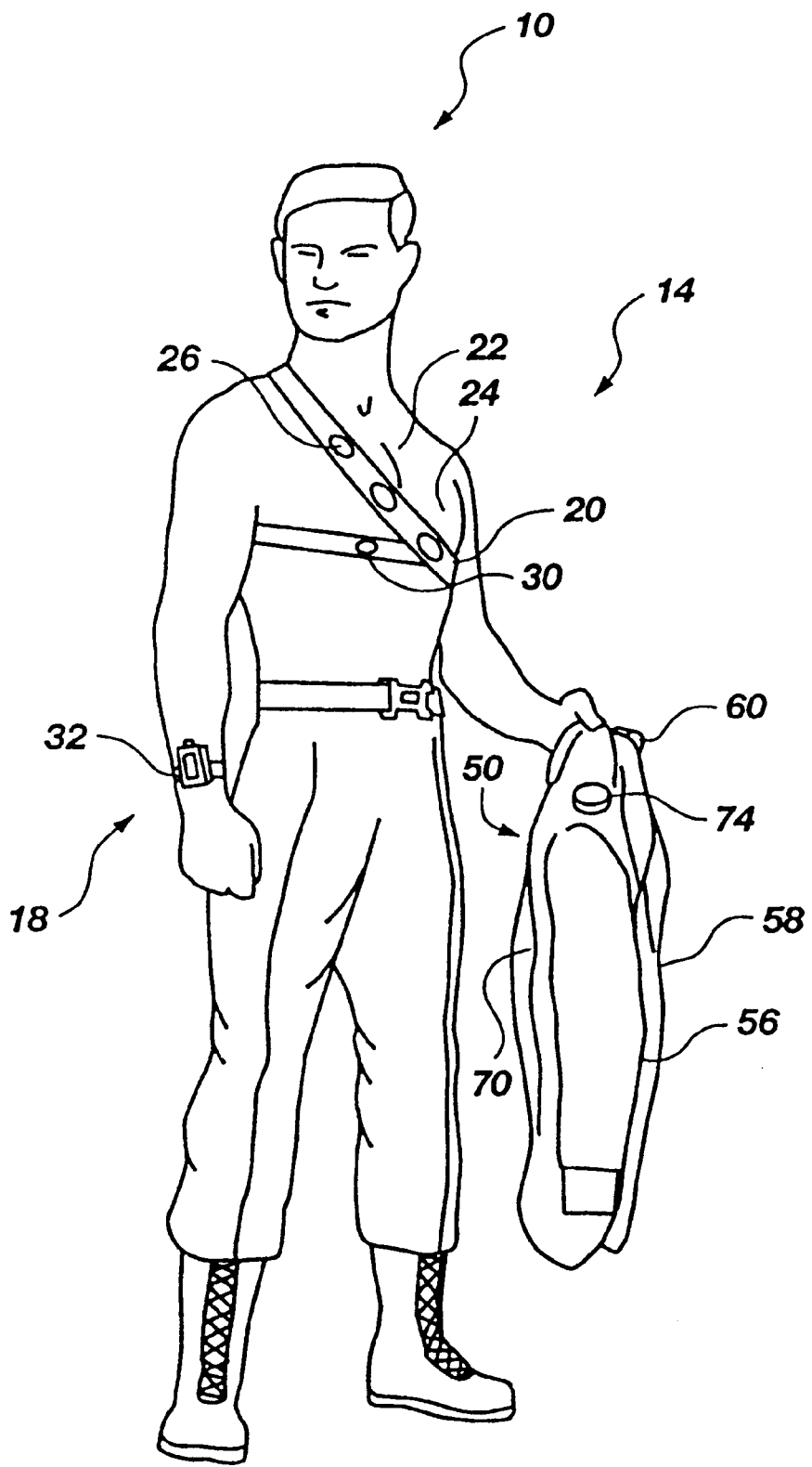
FIG. 1 is a perspective view of a soldier having an integrated sensor unit attached about his chest and a soldier unit disposed within a jacket in accordance with principles of the present invention.

Reference will now be made to the drawings in which the various elements of the present invention will be given numerical designations and in which the invention will be discussed so as to enable one skilled in the art to make and use the invention. Referring to FIG. 1, there is shown a soldier, generally indicated at 10, with an integrated sensor unit, generally indicated at 14, and a wrist sensor/display unit 18 disposed thereon. The integrated sensor unit 14 utilizes a strap which wraps about the soldier's body immediately below the pectoral muscles, and preferably extends over one of the soldier's shoulders. The strap 20 is made from a flexible material which may be worn comfortably for extended periods of time. The use of the elastomeric material sold as SANTOPRENE has been found to work well under a wide range of conditions, and thus is believed to be a preferred material. However, those skilled in the art will appreciate numerous other materials which may be used. Additionally, further research in polymer technology will likely yield additional materials which are particularly suited for such an application.

Disposed in the strap 20 of the integrated sensor unit 14 are a plurality of sensors, identified in FIG. 1 at 22, 24, 26 and 30. While shown in FIG. 1 to have a diameter equal to or greater than the strap 20, the sensors 22, 24, 26 and 30 are typically much smaller, are for the most part embedded in the strap, and would not be visible except upon closer examination of the strap 20.

In the embodiment discussed with respect to FIG. 1, the sensors 22, 24, 26 and 30 of the integrated sensor unit 14 include sensors for determining the ambient temperature (i.e. the temperature under the soldier's clothing, the soldier's body surface temperature, the soldier's heart rate, the soldier's breathing rate, the soldier's position (i.e. whether standing or in a prone position), motion status (i.e. walking or stationary), and whether the soldier is shivering. Additionally, sensors may be included (e.g. blood pressure, breathing rate and oxygen saturation) to determine if the soldier is perspiring, or to detect other physiological data about the soldier. All of the sensors may be contained within the integrated sensor unit 14. Alternatively, some may use other platforms on the body, such as an attachment mechanism to the ear or neck, or disposed in the wrist band 32 of the wrist sensor/display unit 18.

On the wrist of the soldier 10, there is shown the wrist sensor/display unit 18. While sensors may be included as mentioned above, the wrist sensor/display unit 18 is used primarily for viewing information regarding the time and the geolocation of the soldier 10. The wrist sensor/display unit 18 communicates with an executive controller which is discussed below.

Physiological data is conveyed from the integrated sensor unit 14, and wrist sensor/display unit 18 (if so used) to an executive controller of a soldier unit, generally indicated at 50, which is disposed within a harness 56, such as a vest or jacket, of the uniform 58 worn by the soldier 10. Preferably, the harness 56 is part of the conventional load carrying equipment of the soldier.

The soldier unit 50 contained within the harness 56 is responsive to the integrated sensor unit 14 and wrist sensor/display unit 18 in that it receives sensor data and communicates the data to a remote monitoring unit, such as the leader/medic unit and/or the command unit which are discussed in detail below.

The soldier unit 50 is disposed in the uniform 58 to keep it from interfering with the soldier's normal duties. While the soldier unit 50 adds a small amount of weight (i.e. approximately 5 pounds) to the uniform 58, the added functionality of the system more than compensates for the weight. Preferably the soldier unit 50 is disposed in such a way that the soldier will barely notice its presence and his/her performance will not be impaired.

The soldier unit 50 includes an antenna 60 for sending and receiving data from remote locations. Typically, the information will be sent at defined intervals so that a remote monitoring unit, such as a leader/medic unit or a command unit, (both discussed below), can keep track of the physiological status and geolocation of each soldier. Each of these systems, however, also typically includes a communications mechanism for causing the soldier unit 50 to provide the information on demand. Thus, for example, if the sensors in the integrated sensor unit 14 indicate a threat of hypothermia, the leader/medic unit or the command unit may instruct the soldier unit 50 to provide more frequent information about the physiological status of the soldier until the situation is rectified.

To assist in subsequent treatment situations, the soldier unit 50 can have a data storage device which keeps a data record of physiological information for some given length of time, e.g. the last 4 hours. This time period may be fixed or selectable, e.g. mission dependent. Typically, a flash memory card or some other small, compact storage mechanism would be used to store the information. In the alternative, the leader/medic unit discussed below may be provided with sufficient data storage capacity to record such data for all of the soldier units 50 with which it communicates.

Also disposed in the uniform is a global positioning system, generally indicated at 70. The global positioning system 70 is used for geolocation of the soldier 10. By being able to continually monitor the position of the soldier 10, the leader/medic control and the command unit can be used to rapidly find casualties—thus decreasing delay in the treatment of injuries—and can avoid situations in which soldiers are fired upon by their own troops. By knowing the location of each soldier with specificity, the central command center can give instructions to other military units as to how to avoid "friendly fire".

The global positioning system 70 communicates with the leader/medic unit and with the command unit through a communication system, which uses a radio and a second antenna 74 which is typically disposed on the shoulder of the soldier's uniform 58. The radio preferably uses brief bursts of data to prevent enemies from accurately tracking the soldier by monitoring the data transmissions. Those familiar with radio communications will be able to identify protocols which will assist in preventing the signals from being used by enemy forces.

As mentioned above, the antennas 60 and 74 are preferably mounted on or in the shoulders of the soldier's uniform 58. To prevent them from being damaged and/or interfering with the soldier'duties, the antennas preferably have a low profile. In addition to not interfering with the soldier'duties, a low profile antenna will generally suffer from less interference by the soldier's body than will larger antennas. However, other configurations assuring good propagation/reception of signals and minimizing interference by the soldier's body are also acceptable.

Figure 2:
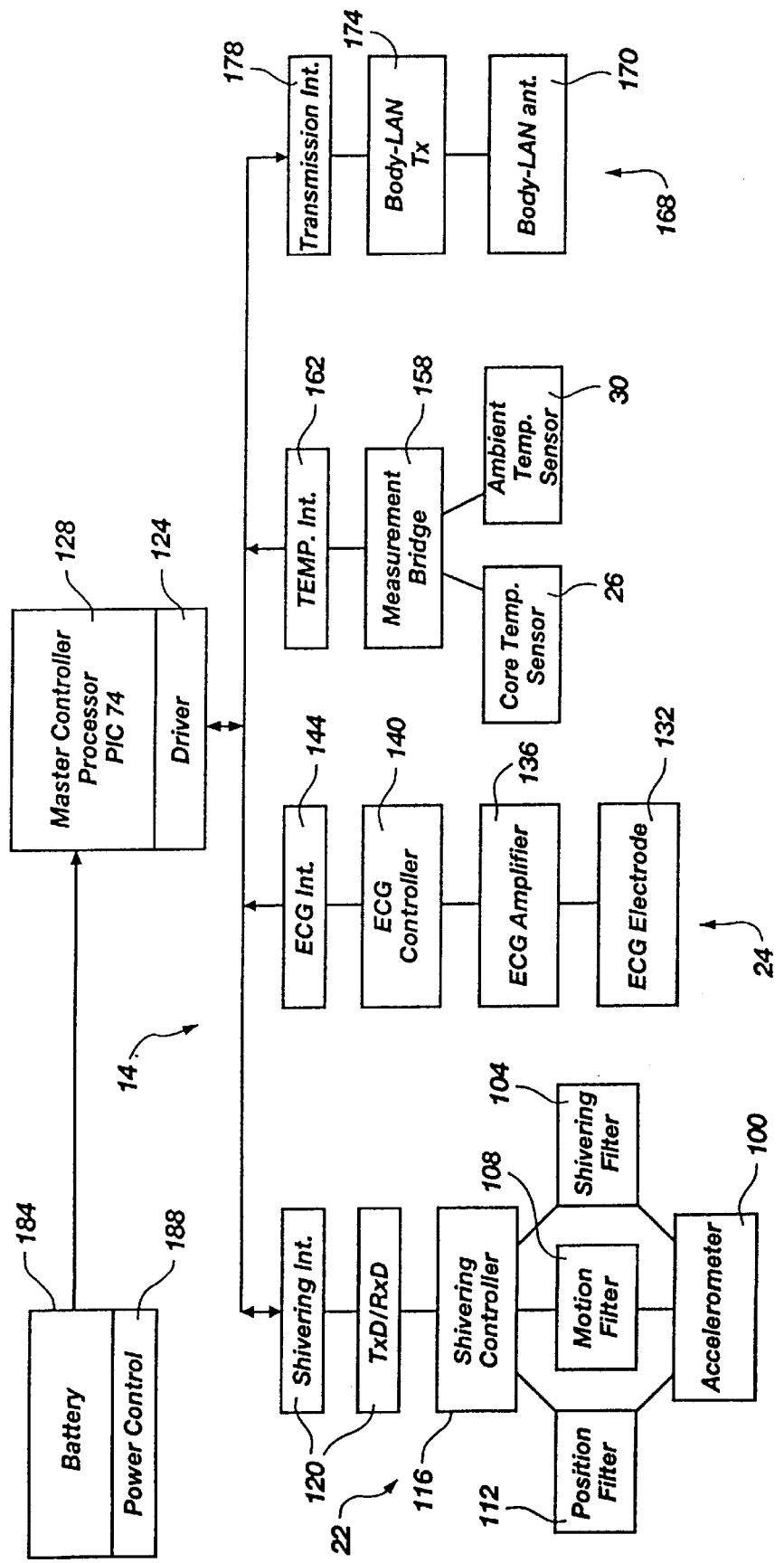
FIG. 2 is a function block diagram of the integrated sensor unit and the sensors contained therein.

Referring now to FIG. 2, there is shown a diagram of the integrated sensor unit 14 and the sensors contained therein. This is an example of possible implementation of the integrated sensor unit functionality and it should be appreciated that other embodiments may be used within the scope of the invention. Beginning at the lower left of the diagram, there is shown a first sensor, generally indicated at 22. The sensor 22 includes at least one accelerometer or acceleration switch 100, the information from which is passed through three filters, indicated at 104, 108 and 112. The first filter 104 is used to determine if the soldier is shivering. The frequency range over which the sensor 22 is monitored is typically between 8 and 12 Hz, and frequency analysis is used to determine if shivering occurs beyond some threshold level. For example, the soldier can be monitored to determine if any shivering occurs for longer than 3 seconds within any given minute interval. By monitoring the shivering of the soldier and frequency thereof, the soldier unit or other units can determine the threat of hypothermia.

The second filter 108 is a motion filter which determines if the soldier is moving or standing still and will typically monitor a range of 0.1 Hz to 5 Hz. By monitoring the motion status of the soldier, in addition to other physiological data, significant information can be achieved about the health of the soldier. For example, a consistently high heart and breathing rate in a soldier who has not moved for an extended period of time could indicate an undesirable physiological condition indicative of injury or illness.

The third filter 112 is used to determine the body position of the soldier. Thus, a remote leader/medic unit or command unit can determine if the soldier is standing or in a prone position. In the alternative, a separate sensor may be used in which a small conductive ball or a sphere of mercury is placed in a spherical cavity. A plurality of wire pairs are disposed in a spherical cavity. A plurality of wire pairs are disposed to extend into the cavity. As the ball or sphere rolls within the cavity, it contacts the wire pairs and thereby indicates position. Such devices are commercially available and have been favorably evaluated.

The information generated by the accelerometer 100 and filters 104, 108 and 112, or by other sensors serving similar functions, is passed through a controller 116 and then through a transmission/interface 120 which communicates through a driver 124 with a master controller or processor 128 where it is processed and forwarded to the soldier status unit. Additionally, the master controller or processor 128 may be used to indicate signals which are indicative of physiological factors not falling within acceptable ranges.

Disposed adjacent to sensor 22 is sensor 24. The sensor 24 includes at least two and preferably three ECG electrodes 132. The electrodes 132 are preferably made from a conductive elastomeric material, such as conductive SANTOPRENE, and provided with horizontal ribs. Of course, other electrodes such as silver-silver chloride electrodes could also be used.

The electrodes are preferably dry and rely on body moisture/oil for conduction. Signals received by the ECG electrodes 132 are passed through an amplifier 136, an R-wave trigger and a controller 140 and then an ECG interface 144 which communicates with the master controller/processor 128 through the driver 124.

A pair of temperature sensors, 26 and 30, are also provided. The sensors include a skin temperature sensor 26 and an ambient (under the clothing) temperature sensor 30. Both of the sensors 26 and 30 will typically be thermistors with the sensor 26 being disposed on the inside of the strap 20 and sensor 30 being disposed on the outside of the strap. A measurement bridge 158 is used to compare the information received by the two sensors 26 and 30. Over a prolonged period of time, the information received can be used to determine the risk of hypothermia or hyperthermia, in addition to cases in which the hypothermic or hyperthermic state has already begun. The measurement bridge 158 communicates with the driver of the master controller/processor 128 through an interface 162.

To facilitate communications between the integrated sensor unit 14 and the soldier unit 50, a local area network or body-LAN 168 is provided. The body-LAN 168 includes an antenna which transmits information received through a transmission device 174 via the interface 178. While wires could be used to facilitate communication between the integrated sensor unit 14 and the soldier unit 50, most soldiers object to the use of wires because they must pass through the clothing and because of the risk that the wire might interfere with mobility under battlefield conditions.

To power the respective sensors, body-LAN 168 and the master controller 128, a battery 184 and a power control 188 are also provided. Typically, the master controller 128 will be programmed to draw power from the battery during predetermined periods only to prolong battery life. For example, the sensors may be powered for 2 seconds of every minute, thereby allowing updating of physiological data with little consumption of power. If the feedback provided by the sensors indicates that there is a threat to the health of the soldier, the leader/medic unit or the command unit can remotely instruct the integrated sensor unit 14 to provide more frequent monitoring and reporting of the soldier's physiological data and status.

Figure 3:
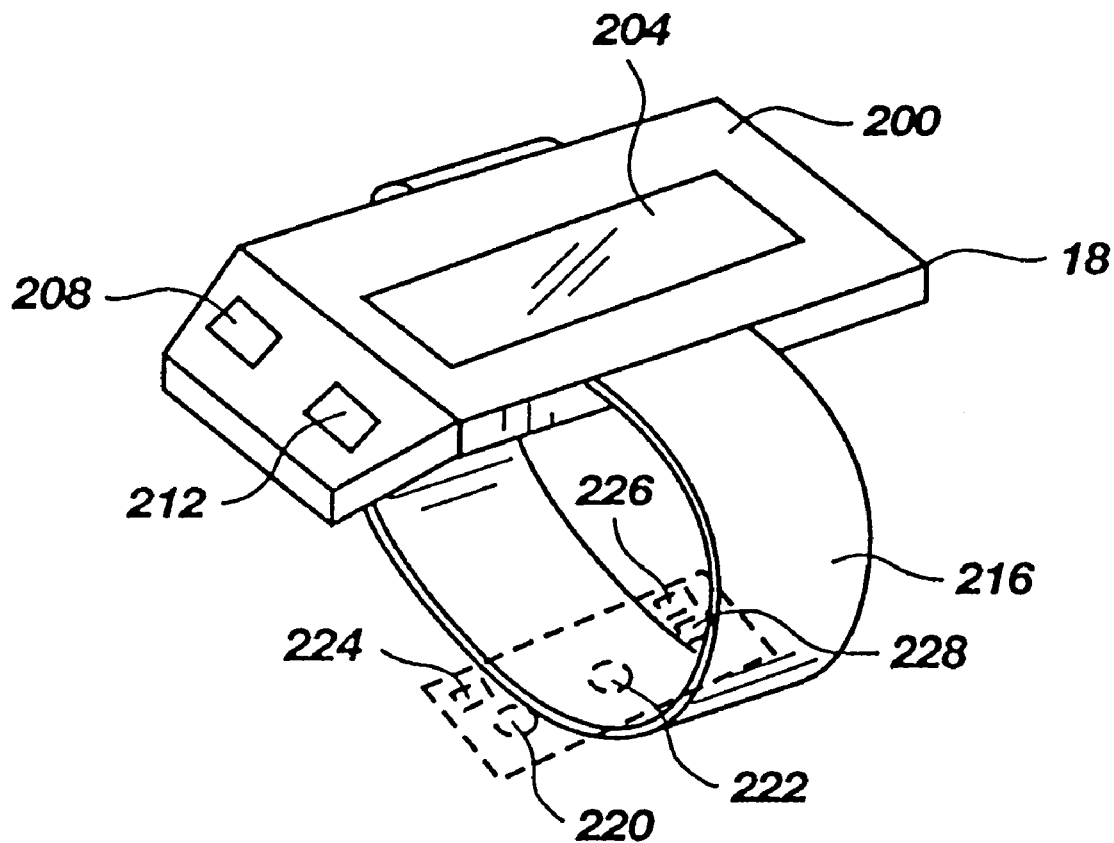
FIG. 3 is a perspective view of a wrist sensor/display unit which may be used as part of the soldier unit.

Referring now to FIG. 3, there is shown a perspective view of the wrist sensor/display unit 18 shown in FIG. 1. The wrist sensor/display unit 18 includes a body 200 with a display screen 204 contained therein. Typically the display screen 204 will be an LCD screen, although other types of displays may be used. The display screen 204 is used to display information regarding time and geolocation, and could even be used to communicate instructions to a soldier regarding his physiological status, or the position or physiological status of other soldiers. A pair of control buttons 208 and 212 are provided to enable the soldier to chose what information is displayed, and to control the LCD illumination when necessary.

The wrist sensor/display unit 18 is held in place with a band 216. If desired, sensors 220 and 222 can be disposed in the band 216 and integrated with the integrated sensor unit 14 FIGS. 1 and 2). Typically, sensor 220 will be a noninvasive blood pressure monitoring system, and sensor 222 will be a sensor for determining oxygen saturation. Other sensors may also be provided for determining environmental variables.

If sensors are provided, the wrist sensor/display unit 18 will also include a communications mechanism 224 for communicating with the integrated sensor unit 14, or with the soldier unit 50, and a controller 226 for processing the information obtained by the sensors 220 and 222, and for operating the display 204. Additionally, a controller 228 may be provided for operating medical equipment, such as a microinfusion pump or a small respirator.

Figure 4:
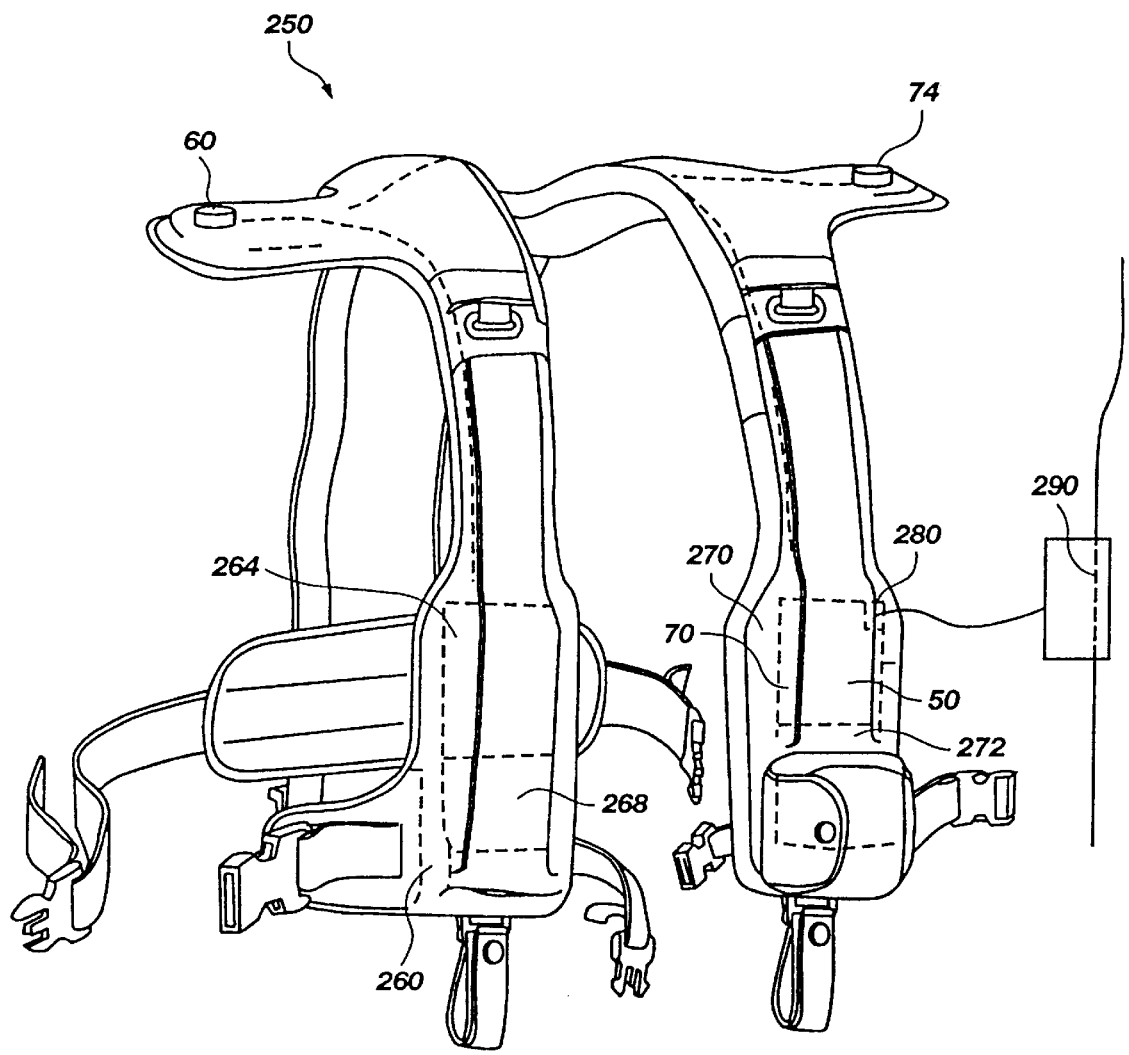
FIG. 4 is a perspective view of a vest/harness configured for holding the soldier status unit.

FIG. 4 is a perspective view of a harness in the form of a vest configured for holding the soldier unit 50. The vest, generally indicated at 250, is configured for use as conventional load carrying equipment similar to those currently used by military personnel. The vest 250 has a first pocket 260 which is configured to receive a radio 264 and a battery pack 268. The radio 264 is connected to the antenna 60 for wireless communications.

Disposed in a second pocket 270 in the vest 250 is a second battery pack 272 and the soldier unit 50. The soldier unit 50 communicates with the integrated sensor unit 14 (FIGS. 1 and 2) via the body-LAN 168 (FIG. 2). The global positioning system 70 can be disposed with the executive controller of the soldier unit 50, or in the pocket 260 with the radio 264. Of course, the global positioning system 70 can be formed as an integral part of the soldier unit 50 if desired.

Regardless of whether the global positioning system 70 and the soldier status unit 50 are formed integrally with one another or not, the units are provided an identification number which allows the leader/medic unit to identify which soldier unit 50 is sending the information. The identification number will also typically be placed on the integrated sensor unit so that the three components form an integrated system for monitoring personnel.

The identification numbers should also be printed on or otherwise attached to the respective components of the system for monitoring personnel to facilitate identification by the person to which it has been assigned. Preferably, no two soldier status units will ever receive the same identification number, thereby preventing the situation in which the leader/medic unit or the command unit confuses the data obtained from two or more soldier units 50.

As shown in FIG. 4, the soldier unit 50 also includes a medical device driver interface 280. The interface 280 allows the soldier status unit 50 to control a micromedical device 290 such as an IV volume replacement pump or a drug delivery pump. Examples of such pumps are disclosed in U.S. Pat. No. 5,632,606 and related applications for a Volumetric Pump, which is expressly incorporated herein.

When a soldier is injured, the interface 280 allows the soldier unit 50 to control a small medical device in accordance with a protocol downloaded from a leader/medic unit to the soldier unit. Thus, a medic can set up an IV or drug delivery apparatus for a soldier and then leave to attend to other casualties. The soldier unit 50 ensures the proper amount of IV solution or drug is administered without the need for constant checking by the medic. The information received by the soldier status unit 50 from the integrated sensor unit 14 (FIGS. 1 and 2) via body-LAN transmission can be used to modify the medical device to obtain more efficacious treatment. Additionally, the information with respect to the volume of IV solution or amount of the drug which has been infused can be relayed to the leader/medic unit or the command unit for verification and recording for subsequent use by medical personnel.

In the alternative, the medical device 290 could be a small ventilator used to ensure that the soldier is receiving enough oxygen. Information regarding breathing rates, etc., can be relayed by the soldier status unit 50 to the leader/medic unit and/or the command unit, and the ventilator may be remotely controlled to respond to changing physiological conditions.

Disposed the soldier status unit 50, global positioning system 70, the radio 264 and the battery packs 268 and 272 in the vest 250 is advantageous because it causes no interference or minimal interference to the soldier. The vest 250 is used in place of and fulfills all other functions of the standard load carrying equipment harnesses commonly worn by soldiers in combat, while simultaneously containing the soldier unit 50 and all of its components, e.g. the global positioning system 70.

Figure 4A:
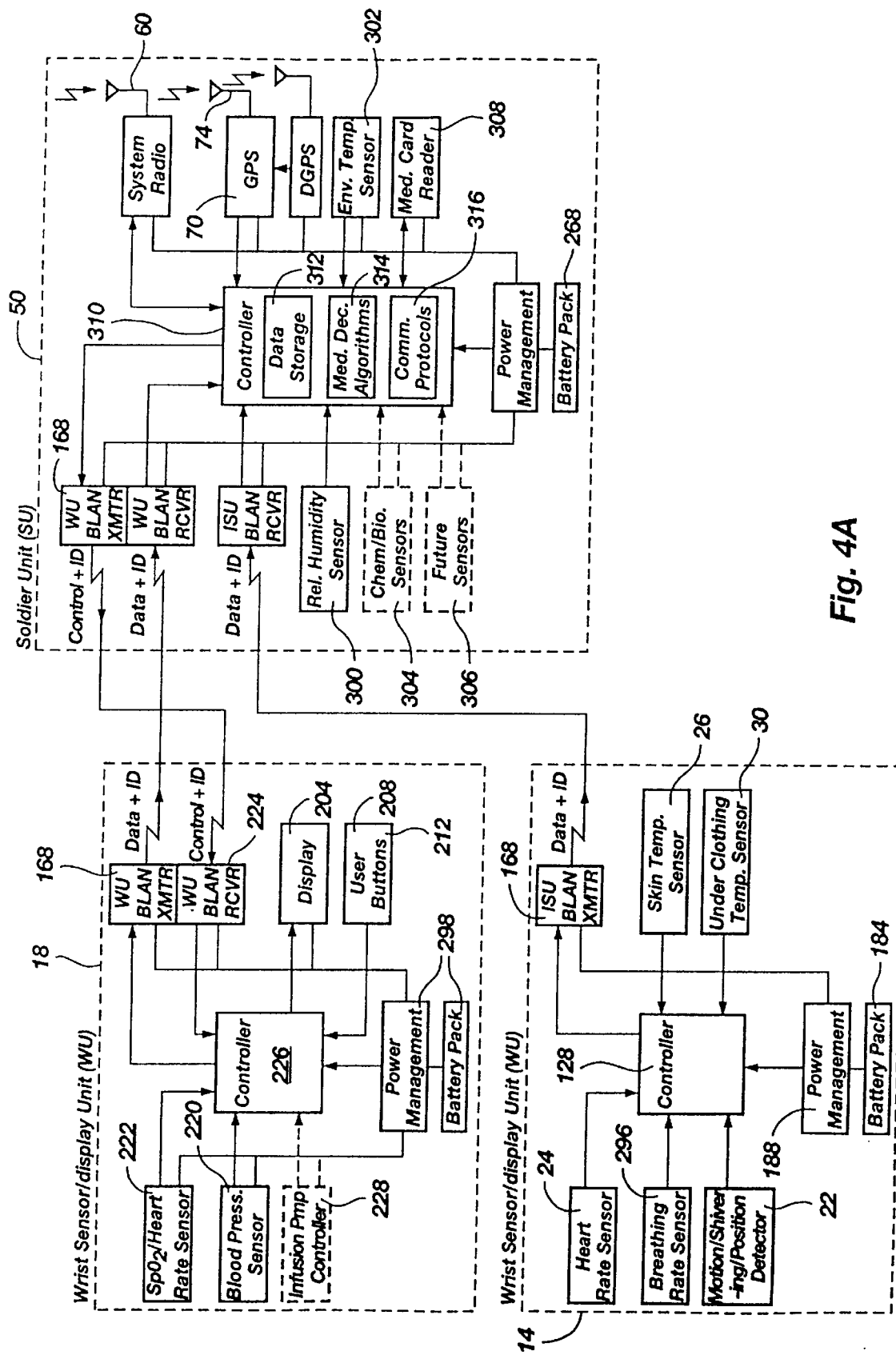
FIG. 4A is a function block diagram of the interactive arrangement between the integrated sensor unit, the wrist sensor/display unit and the soldier unit.

Referring to FIG. 4A, there is shown a function block diagram of the integrated sensor unit 14, the wrist sensor/display unit 18, and the soldier unit 50.

The sensor array of the integrated sensor unit 14 is substantially the same as set forth in FIG. 2, except that a breathing rate sensor 296 has been added. As will be appreciated, as sensor technology improves and facilitates the use of smaller, less energy consumptive sensors, the number of sensors which may be practically included in the integrated sensor unit can be increased. Such sensors could also be modularly connected to either the integrated sensor unit 14 or to the wrist sensor/display unit 18 such that sensors could be added when needed, and then removed to enable the use of still other sensors.

The wrist sensor/display unit 18 shown in FIG. 4A contains all of the same elements described above, except that the power management battery combination 298 is shown, and the communications mechanism 224 is shown in additional detail. The communications mechanism 224 forms part of the body local area network 168. By providing for a wireless body-LAN 168, the integrated sensor unit 14 and the wrist sensor/display unit 18 are able to communicate with the soldier unit 50 without interfering with the ability of the soldier to perform his/her duties. Because the respective components are so small, they provide minimal interference to the soldier, while simultaneously reducing the risk of death or serious injury.

While both the integrated sensor unit 14 and the wrist sensor/display unit 18 communicate through the body-LAN 168, the involvement of the communications are different. Because the integrated sensor unit 14 simply senses physiological status and generates signals indicative of the same, the integrated sensor unit will typically only send signals to the soldier unit 50. In contrast, because the wrist sensor/display unit 18 displays information regarding position can can include a controller 228 for controlling other medical equipment such as a microinfusion pump or a ventilator, it is important for the wrist sensor/display unit to be able to both send signals to and receive signals from the soldier unit 50. Thus, the communications mechanism 224 of wrist sensor/display unit 18 has both a transmitter and receiver.

In addition to all of the sensors which may be contained in the integrated sensor unit 14 and the wrist sensor/display unit 18, the soldier unit 50 can include a plurality of additional sensors for providing information to the leader/medic unit and/or the command unit. For example, in FIG. 4A, the soldier unit 50 includes a relative humidity sensor 300, and an environmental temperature sensor 302. As sensor technology improves, sensors 304 will be added for detecting chemical and biological warfare agents, and other sensors 306 as may be developed in the future. An input mechanism, such as a medical card reader 308 is also provided to download necessary information.

The information from the sensors is processed in the controller 310 which accesses data storage 312, includes software or firmware with medical diagnosis algorithms 314, and communications protocols 316 to store relevant information, to communicate needed information to the leader/medical units and command units. When the signals conveyed indicate problem situations, help may be dispatched, the controller may produce an audible or other alarm, and/or instructions may be sent to the soldier's display 204 on the wrist sensor/display unit 18.

Figure 5:
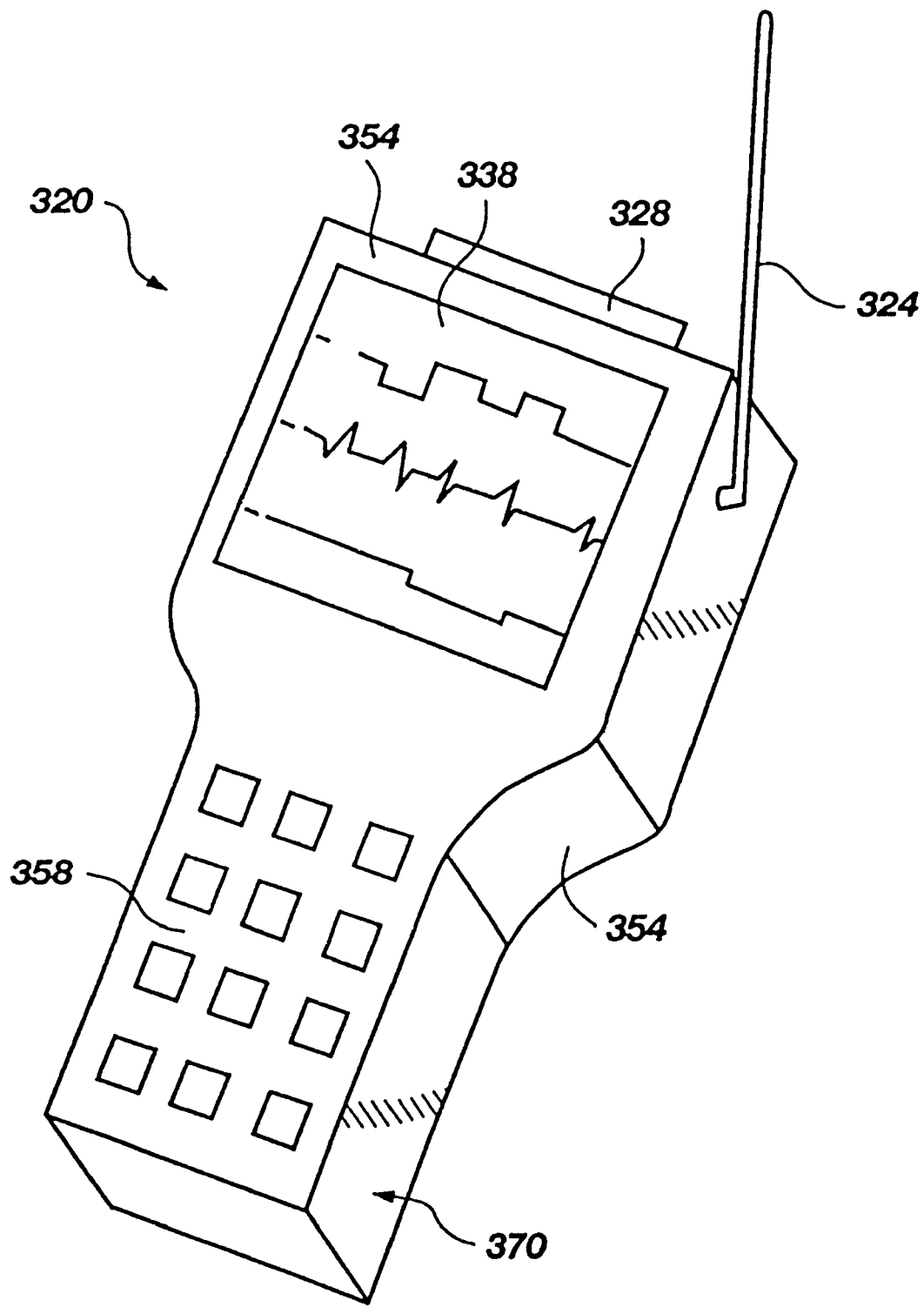
FIG. 5 is a perspective view of a leader/medic unit for use by leaders and medics to locate and communicate with the soldier units of the present invention.
Figure 5A:
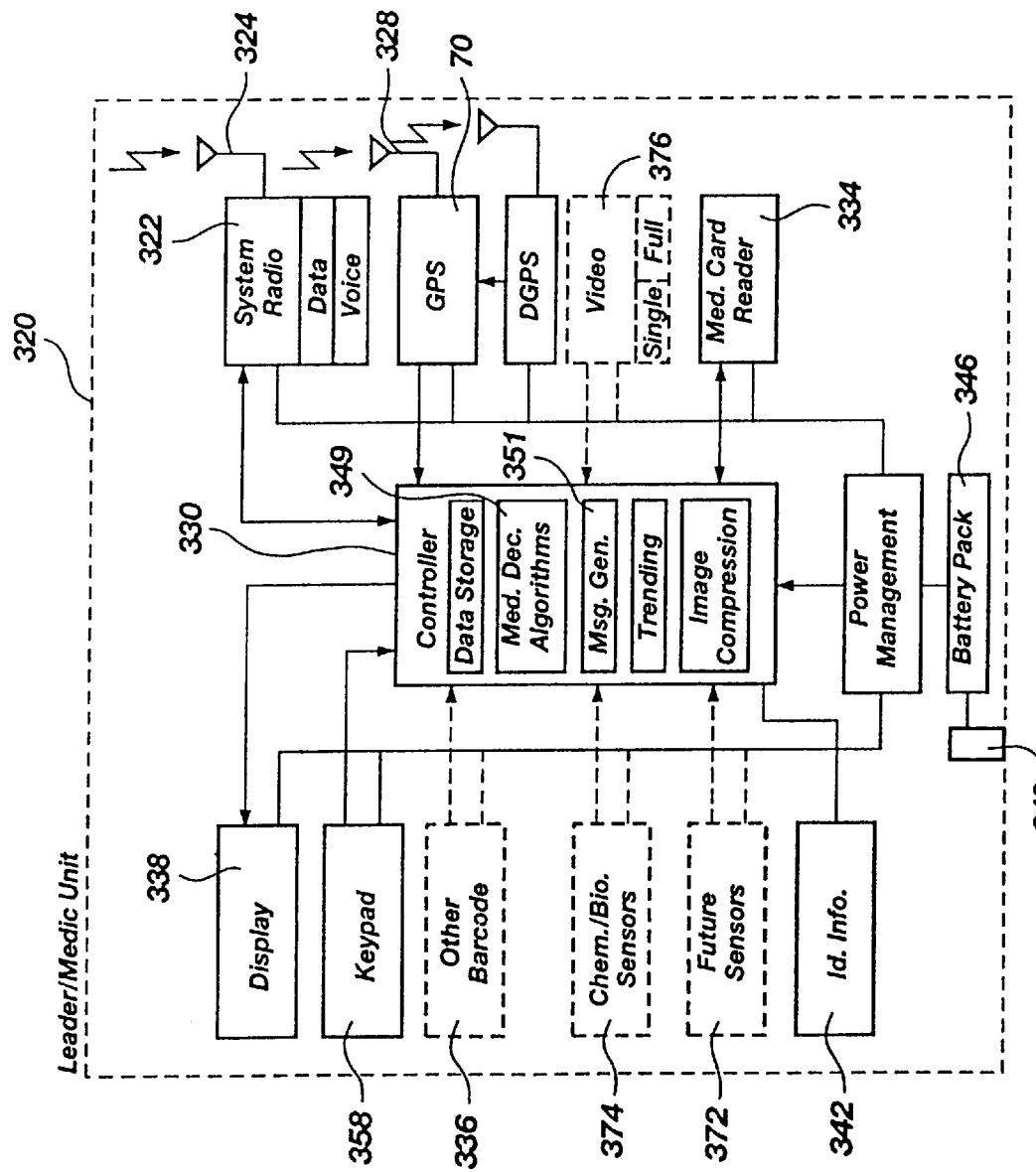
FIG. 5A is a function block diagram of the leader/medic unit of FIG. 5.

Referring now to FIGS. 5 and 5A there is shown the components of a leader/medic unit 320. The unit includes a radio transceiver 322 which is connected to an antenna 324 to enable the leader/medic unit 320 to communicate with a communications system allows for the transfer of data packets between system units. The radio transceiver 322 also allows for the downloading of software and the reporting of current software in the leader/medic unit 320. A second antenna 328 is provided to facilitate communications by the global positioning system 70 which is integrated in the leader/medic unit.

The leader/medic unit 320 is controlled by a micro-computer or similar controller 330. The micro-computer 330 includes an externally accessible port 334 which can be used to download software or other information to the micro-computer and communicates directly with the micro-computer by hardwire. As shown in FIG. 5A, the port 334 is used to read medical cards having a magnetic data strip. A bar code reader 336 or other similar device may also be used for entering precoded information.

Also disposed on the leader/medic unit 320 is an identification number 342 which corresponds with an identification number programmed into the electronics to provide a remote device assurance that the proper unit has been contacted. As with the identification numbers of the soldier units, it is preferable that no two identification numbers ever be the same.

The global positioning system 70 mentioned above is integrated with the leader/medic unit 320 so that it may be controlled by the micro-computer. Preferably, the micro-computer 330 control the on/off mechanism to the global positioning system 70 to decrease power consumption. A battery 346 supplies the power to both the global positioning system 70 and the micro-computer 330. The battery 346 may be disposable, or a recharging adapter 348 may be provided. To maximize battery life between changes or recharges, both hardware and software power control measures are used.

Also stored in a memory unit 349 of the micro-computer of the leader/medic unit 320 is software/firmware which can be used to provide basic diagnosis of medical conditions. The leader/medic unit 320 preferably stores a minimum of four hours of history data in the memory unit 349 and sounds an audible alarm or generates some other message 351 in the event that one or more defined thresholds are exceeded.

The micro-computer 330 of the leader/medic unit 320 collects information from all of the soldier units 50 which are assigned to it. To ensure that the leader or medic is properly monitored, each leader or medic will typically wear a soldier unit in addition to carrying a leader/medic unit 320.

As is shown in FIG. 5, the leader/medic unit 320 is configured for operation by one hand. The leader/medic unit 320 includes a housing 354 which is small enough to be comfortably held in one hand. A keyboard 358 is provided to enable the leader/medic to input information, and to control what information is displayed on the LCD display 338. The unit leader may use the display 338 to monitor the position of soldiers in a particular unit, wile the medic may use the display screen initially to locate an injured soldier, and then to monitor physiological data received from the integrated sensor unit of a soldier status unit 50.

When a soldier is trained to be a member of the special forces (i.e. Airborne Rangers, Seals, etc.), he is subjected to extreme environmental conditions. For example, if the tasks require prolonged submerging in cold water, hypothermia can quickly set in and place the soldier's life at risk. If the leader/medic unit 320 indicates that the cold, heat, exertion, etc. to which the soldier is being subjected is too much for the soldier to physiologically handle, the commander can remove the soldier from the situation. In such a manner the physical stamina of the prospective combatants can be properly evaluated while providing a mechanism for terminating the test before the soldier's health is adversely affected.

In cases involving casualties, there is often a short period of time, commonly referred to as the "golden hour", during which treatment can significantly decrease the risk of death or permanent disability. By helping the medic to locate the wounded soldier and to diagnose the soldier's injuries, a considerable amount of time is saved, and significantly more soldiers can be treated within that "golden hour".

For the medic, the leader/medic unit 320 provides a significant improvement in triage ability. When a soldier has been wounded the medic can use the small, hand-held leader/medic unit 320 to first determine the casualty's location. The medic then uses the leader/medic unit 320 to determine if the casualty is alive or dead. Those familiar with combat will appreciate that many lives are lost in combat attempting to treat or retrieve soldiers who are already dead. By determining the status of the soldier in advance, additional lives may be saved by having the medic focus on those who are best able to benefit from immediate treatment.

If the casualty is alive, but not reachable, the medic may contact other troops who are closer to the casualty, or may request air support to pick up the wounded soldier. If the wounded soldier is near enough to the medic, the medic uses the display screen 338 of the leader/medic unit 320 both to navigate and to conduct an en route examination as to the soldier's condition.

To ensure an accurate diagnosis, constant updating of the physiological information is necessary. Thus, the leader/medic unit 320 can instruct an individual soldier unit 50 to send information about the physiological status of the soldier to whom it is attached. The information appears on the display screen 338 of the leader/medic unit 320 and allows the medic to know the important physiological information about the casualty before the soldier is reached. By the time the medic reaches the soldier, he may have a preliminary course of treatment determined, and may have already communicated with a central command post to arrange transport of the soldier is necessary.

Preferably the display screen 338 used by the medic or by a leader is large enough to shown a map of a particular area so that the position of each soldier whose soldier unit is assigned to the hand-held unit may be displayed. In the event that a soldier is wounded, suffering from hypothermia, etc., the screen provides an indication to the medic or leader that help is needed by that soldier. The user of the leader/medic unit 320 may then use the keyboard 358 to select from the available information, or to input information when necessary. For example, a medic may input information into the leader/medic unit 320 regarding care given to a soldier. The information may then be conveyed to a command unit and/or to the soldier unit 50 of the soldier from where it may be accessed as the soldier is moved to higher levels of care. In the alternative, each soldier may have a card or other device with a data storage medium for recording such information.

The identification numbers for a group of soldiers units 50 are also loaded onto the micro-computer 330, thereby assigning a selected leader/medic unit 320 to the soldier units entered. Preferably the system includes a storage medium, such as a hard drive, flash memory card, etc., for storing history data collected from the assigned soldier units. If necessary, the information can be accessed during treatment of any given soldier.

Referring now specifically to FIG. 5A, the micro-computer 330 can also operate several other devices. As electronics continue to be reduced in size and require less energy, the additional sensors 372, such as chemical and biological warfare sensors 374 can be added to the leader/medic unit 320. Additionally, other types of information gathering equipment, such as a video camera, may also be included. Such a feature will be especially beneficial to medics who will be able to transmit images of wounds, etc., for additional input from medical personnel at a central command center. To facilitate transmission of the information, the micro-computer 330 includes circuitry for image compression.

An additional feature of the leader/medic unit 320 is that of trending. Rather than merely monitoring the physiological data regarding an individual, the micro-computer 330 analyzes and follows trends in the data. Thus, for example, while breathing rate or blood pressure will typically be high for a couple of minutes after a solider has performed some physically strenuous task, a consistently increasing breathing rate or blood pressure while the soldier is not moving may indicate an undesirable physiological state and indicates a need to contact or otherwise monitor the soldier.

Figure 6:
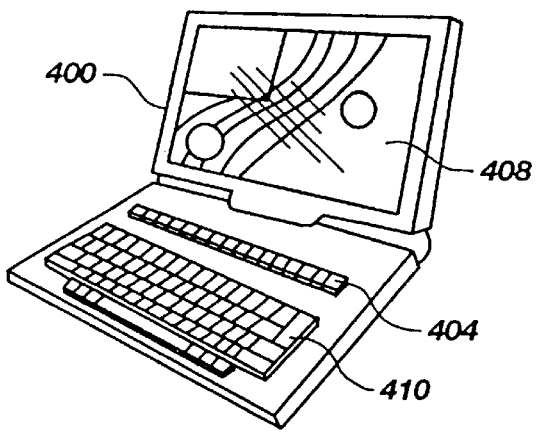
FIG. 6 is a perspective view of a command unit of the present invention for locating and communicating with the soldier status units and leader/medic.
Figure 6A:
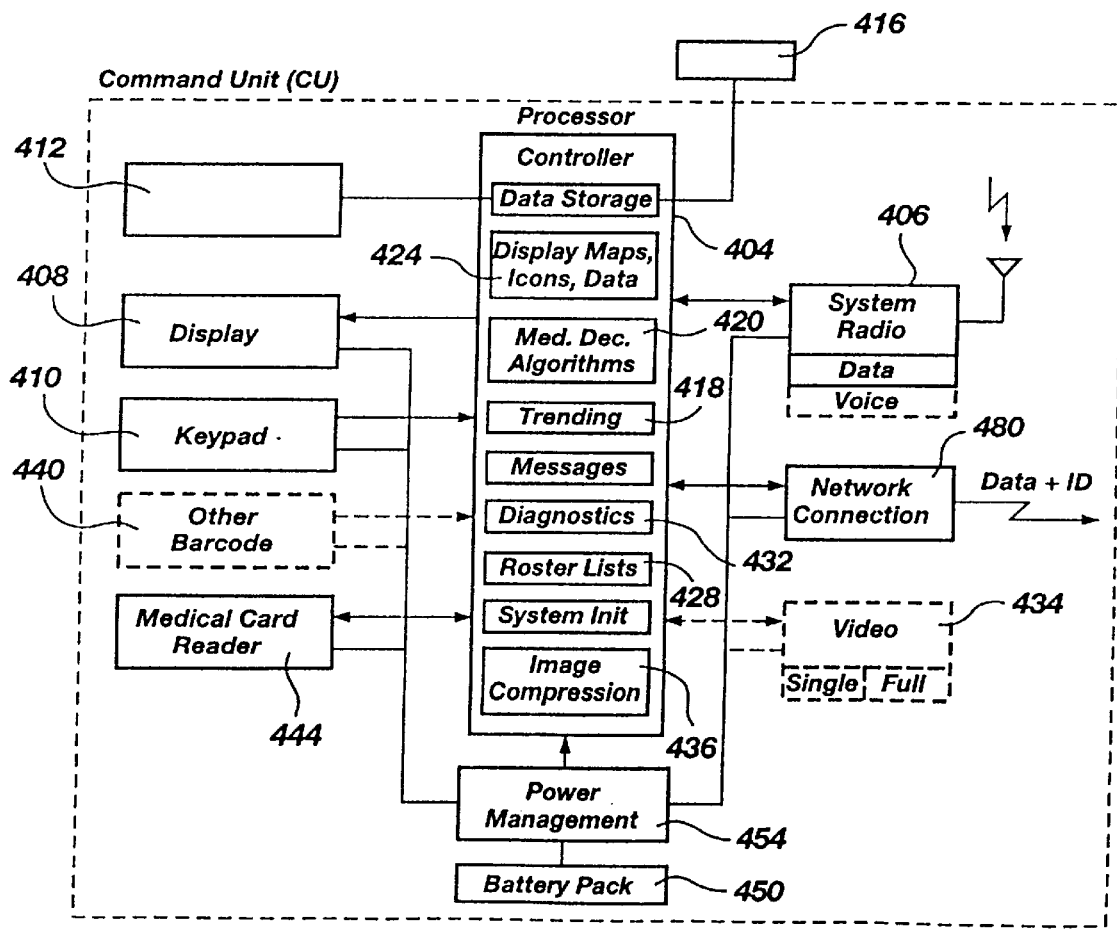
FIG. 6A is a function block diagram of the command unit shown in FIG. 6.

Referring now to FIGS. 6 and 6A, there are shown a perspective view and a function block diagram of a command unit 400 which is used to locate and communicate with both the leader/medic units 320 and soldier units 50 of the present invention. The unit 400 includes a processor 404 which is connected with a communications means 406. The communications means 406 will preferably be a transceiver disposed within the command unit 400, but may be an external receiver or other device.

The command unit 400 has a display screen 408 which enables a user to track the movement of multiple forces. The user will typically choose an area which he or she desires to monitor, and the processor 404 will use the communications means to signal the individual soldier units 50 and the leader/medic units 320 to determine and indicate their location on the display screen 408. The signals received by the processor 404 from the soldier units 50 and the leader/medic units 320 are then displayed on the display screen 408 in a user friendly manner, e.g. icons, so that the user of the command unit can view the position of the each soldier with respect to others in the area. The user may thus determine the location of all soldiers having a soldier status unit at any location. By monitoring the location of troops and their targets, persons operating the command unit 400 can prevent friendly forces from firing on each other and more efficiently direct troop movements on the battlefield.

In addition to monitoring the location of each soldier, the command unit 400 enables those at a central command site to monitor the physiological status of each soldier represented by an icon. Thus, for example, an icon may flash if the physiological information received from a particular soldier unit is not within desirable ranges. To look at any soldier's physiological status in detail, the user can switch to another level of display by, e.g., selecting the soldier's icon, and the display screen will then provide the desired information about the soldier. Input to the processor 404 is typically done by either a keyboard 410 or a mouse (not shown).

The command unit 400 will also typically include a data storage device 412, such as "hard drive" which is sufficiently large to maintain physiological and geolocation data for each soldier for a prolonged period of time, e.g. 48 hours. If the information becomes relevant for treatment, it can be quickly accessed by either the command unit 400 or the leader/medic unit 320. A larger, long-term data storage device 416 can be used to periodically store data from the storage device 412. The data on the long term storage device 416 may be used for training purposes or for analysis to determine additional methods for decreasing casualties during battle and/or optimizing the safety of training exercises.

In addition to having all of the abilities contained in the leader/medic units 320, the command unit 400 can record all of the historical data received from the soldier units, and can send text or image-based messages back to the leader/medic units 320, or the individual troops via the display 204 on the wrist sensor/display units 18. Thus, the command unit 400 can send messages to the display screen 204 on the wrist sensor/display unit 18 to communicate with soldiers with whom audible communications are unadvisable, such as soldiers caught behind enemy lines.

To ensure that none of the devices may be used against the soldiers if captured by the enemy, each device may contain a self-disabling means, such as software which requires the entry of a password or some other code. If the wrong password is entered for more than one attempt, the device will automatically disable itself. While disablement will not be critical for soldier units, it is important that leader/medic control units and command units not be usable by an enemy to track the position of the soldiers which are monitored by those units.

The processor 404 of the command unit 400 can perform trending 418 as discussed above, and has access to medical decision algorithms 420, geographical mapping information 424, roster lists 428, and other diagnostic software 432. When video input 434 is provided, the processor 404 will also include access to decompression software 436 for viewing on the display 408 or on peripheral devices.

To assist in the downloading of information into the processor 404, data import ports such as a bar code reader 440, a medical card reader 444, or other types of data transfer mechanisms can also be provided.

Power to the unit is supplied by rechargeable batteries 450, and power management software may be provided to maximize battery life while providing adequate power for each of the functions described above.

To further promote the sharing of information received, the command unit 400 may also include a conventional network interface 480 for communicating with other command units, or with computers which are otherwise not connected to the system.

Figure 7:
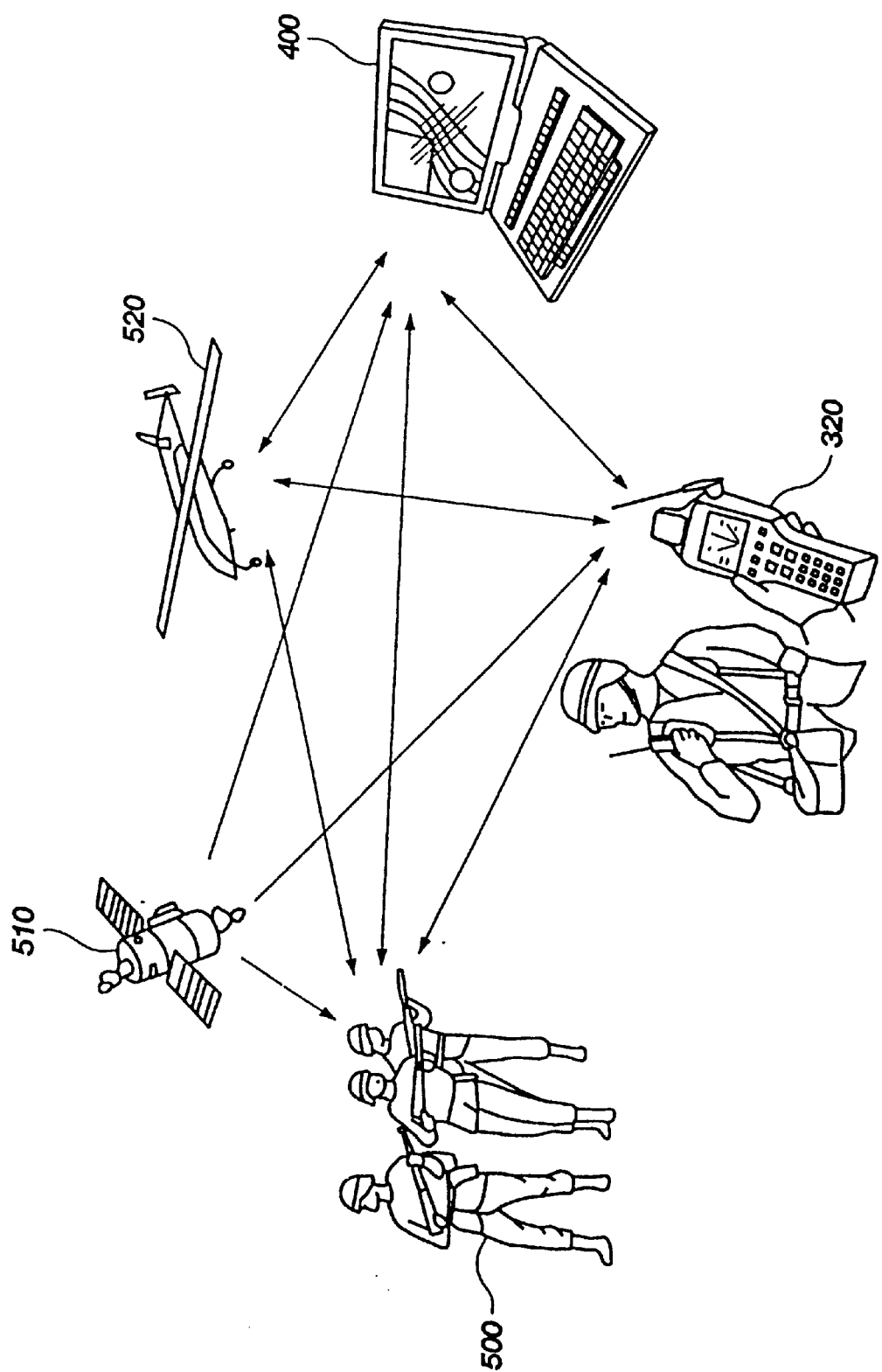
FIG. 7 is a perspective view of the system for monitoring personnel of the present invention, including numerous different forms of communication relays.

Referring now to FIG. 7, there is shown a perspective view of the system for monitoring the status of personnel of the present invention, including numerous different forms of communication relays. When soldiers 500 are using the soldier units, numerous different communications mechanisms should be provided to ensure proper communication between the soldier units 50, the leader/medic units 320 and command(s) 400. Because soldiers are constantly changing location and moving across varying terrain, the system for remotely monitoring personnel status can include satellites 510 and aircraft 520 as relays to assist in communications between the individual soldiers and the command structure. The use of several different communications media allows for continued communication even when the position of the soldier(s) changes in such a manner as to interfere with communications through a single source.

Figure 7A:
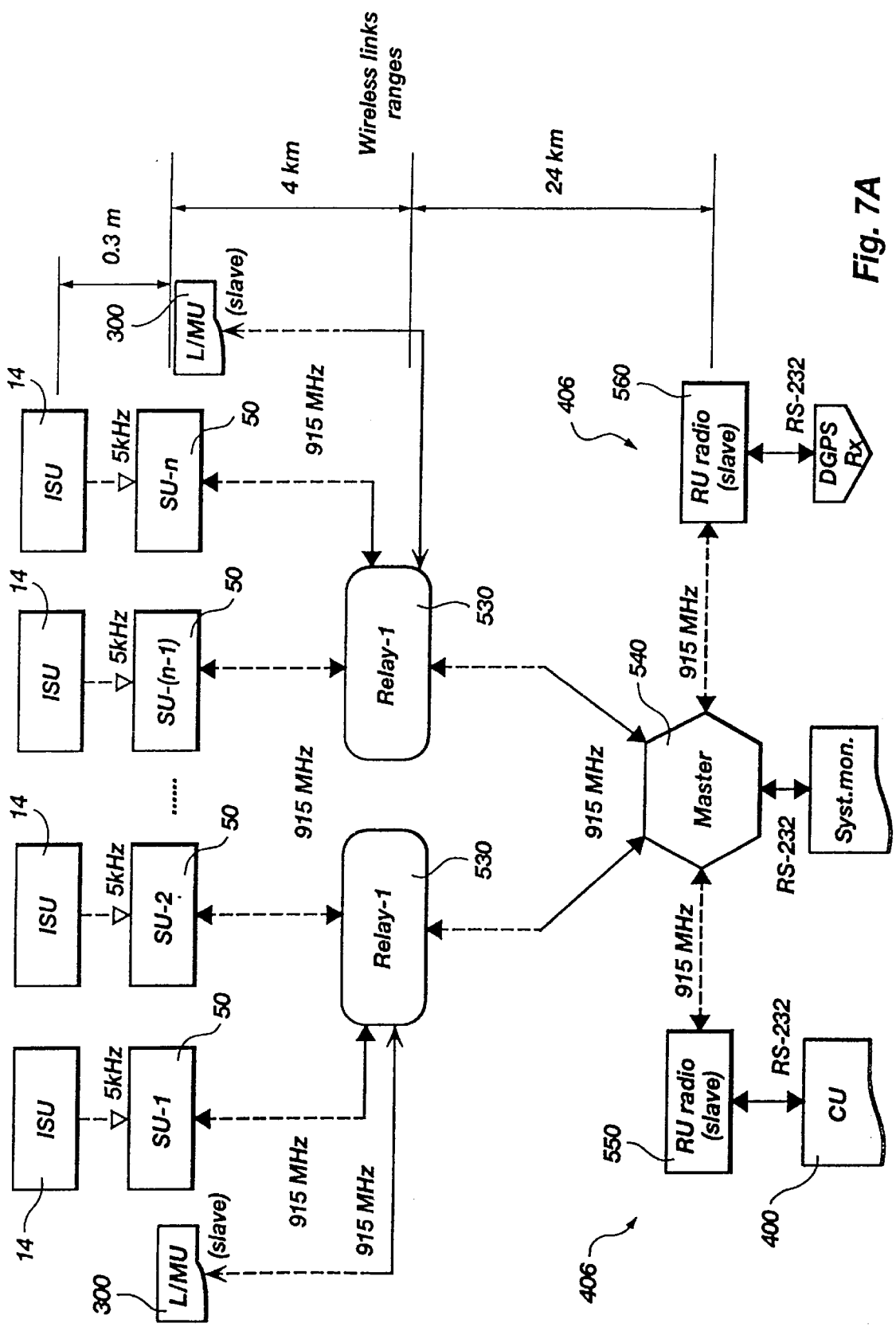
FIG. 7A is a function block diagram of the communication relays, etc. shown in FIG. 7.

Referring now to FIG. 7A, there is shown a function block diagram of the present invention. The system shown includes a plurality of integrated sensor units 14. Each integrated sensor unit 14 communicates with a soldier unit 50 to which the integrated sensor unit is assigned. Communication between the sensor units 50 and the leader/medic units 320 is usually sent through a relay 530, which may be a satellite 51 (FIG. 7), an airplane 520 (FIG. 7) or some stationary structure. The relay 530 also assists in communications between the command unit 400 and the soldier units 50 and leader/medic units 320. The relay is controlled by a master 540 which communicates with one or more slaves to receive signals regarding the physiological status of soldiers and the location. These structures may be part of the communications means 406 of the command unit 400, or may be housed in a separate apparatus, with the signals being sent to the command unit 400 by UHF or some other type of signal. Those skilled in the art will recognize numerous different mechanisms for accomplishing such communications in light of the present disclosure.

Figure 8:
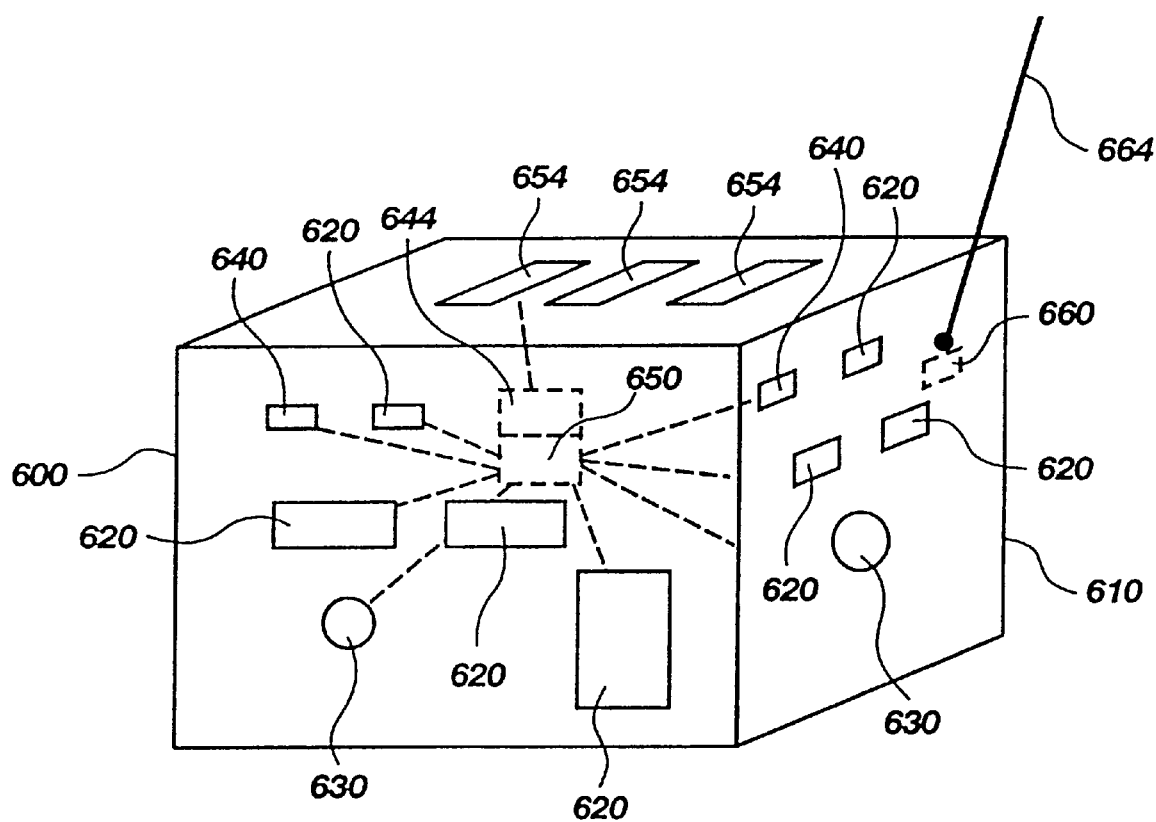
FIG. 8 is a perspective view of a sensor probe which may be used with the system for remote monitoring of personnel to monitor battlefield conditions.

Referring now to FIG. 8, there is shown yet another aspect of the present invention. A sensor probe, generally indicated at 600, is used for conducting remote surveillance and for remote monitoring of an area, regardless of whether any soldiers are present. The sensor probe 600 includes a small housing 610 which will typically be small enough to be held with a single hand. Disposed in the housing are a plurality of sensors 620. The sensors will be disposed to monitor a wide variety of environmental and other factors. For example, an accelerometer may be used to detect the presence of heavy artillery in the area. Chemical and biological warfare agent sensors are used to detect the presence of such agents and to allow for rapid warming to the soldiers. One or more camera lenses may be provided as "sensors" to provide optical images of the area being monitored. Microphones 640 may be provided to provide the ability to remotely monitor sound about the sensor probe 600. Additional sensors can include heat and infrared sensors, temperature sensors, and motion sensors.

While the sensor probe will typically have a battery 644 and a micro-computer 650 which controls the sensors and regulates power consumption, a plurality of solar conversion panels 654 may be used to supplement the power supply and extend the length of the battery.

The sensor probe 600 communicates with the remainder of the system via a transceiver 660 which is connected to the micro-computer 650 and to an antenna 664. When information is desired by a command unit, the micro-computer 650 activates the appropriate sensor(s) and relays the desired information.

In such a manner, the command unit 400 can monitor such conditions as the temperature, the amount of artillery which is impacting an area, the presence of chemical or biological warfare agents, and any other needed information for which the sensor probe 600 has been configured. The sensor probe 600 may used for additional safety—i.e., to act as an additional sentry during the night to prevent surprise enemy attack. Likewise, the sensor probes 600 can be placed by scouting soldiers to monitor an area into which the main units are advancing. Furthermore, the sensor probes could be dropped into areas controlled by the enemy to provide additional information of enemy movements. etc.

Numerous modifications can be made to the present invention without departing from the scope or spirit of the same. For example, an individual status unit could be made smaller and provided to residents of long-term care facilities. The size of the device could be reduced because it need not be as durable as the military version, and would require a much smaller range for radio communications. Rather than requiring nurses to track down patients to take their vital signs, the system for remotely monitoring personnel status of the present invention would enable nurses to determine the patients' location, as well as their vital signs. If the information received indicated a problem, the location of the patient could be readily determined. Thus, a smaller number of nurses could be used while providing a higher level of care.

Thus there is disclosed a system for remotely monitoring personnel status which significantly improves the chance of survival for injured soldiers. Those skilled in the art will recognize numerous modifications which can be made without departing from the scope or spirit of the present invention. The appended claims are intended to cover such modifications.

What is claimed is:

1. Wearable apparatus for monitoring physiological parameters of a person comprising:
   support means for wearing by a person on one or more body parts, the support means comprising a harness having a plurality of pocket means;
   sensor means disposed on the support means for measuring multiple physiological parameters of the person;
   means disposed in at least one of the pocket means and responsive to the sensor means for transmitting to a remote location data indicating values of each of the multiple physiological parameters measured; and
   at least one antenna means disposed on the harness and in communication with the means for transmitting.

2. The wearable apparatus of claim 1, wherein the harness comprises a vest, and wherein the means for transmitting is disposed within the vest.

3. The wearable apparatus of claim 1, wherein the apparatus comprises a global positioning means disposed in the at least one pocket and in communication with the at least one antenna means.

4. The wearable apparatus of claim 1, further including a strap disposable about the person under the harness, said sensor means being disposed in the strap.

5. The wearable apparatus of claim 4, wherein the apparatus further comprises a wireless network means for conveying data from the sensor means to the means for transmitting.

6. The wearable apparatus of claim 1, wherein the support means comprises a strap mountable about the person's torso.

7. The wearable apparatus claim 6, wherein the strap includes a plurality of sensors.

8. The wearable apparatus of claim 7, wherein the support means comprises a band mountable about the person's wrist.

9. The wearable apparatus of claim 8, wherein the band includes a plurality of sensors.

10. The wearable apparatus of claim 1, wherein the sensor means comprises an accelerometer and a plurality of filters disposed in communication with the accelerometer.

11. The wearable apparatus of claim 1, wherein the sensor means comprises an acceleration switch.

12. The wearable apparatus of claim 1, wherein the sensor means comprises a heart rate sensor including ECG electrodes.

13. The wearable apparatus of claim 1, wherein the sensor means comprises a heart rate sensor including an ECG sensor.

14. The wearable apparatus of claim 1, wherein the sensor means comprises a body surface temperature sensor.

15. The wearable apparatus of claim 1, wherein the sensor means comprises an ambient temperature sensor.

16. The wearable apparatus of claim 1, wherein the means for transmitting comprises a receiving/sending means for receiving data indicating the values of the multiple physiological parameters detected by the sensor means, and for communicating said data to remote locations.

17. The wearable apparatus of claim 16, wherein said receiving/sending means comprises a wireless local area network for receiving data from the sensor means.

18. The wearable apparatus of claim 16, wherein the means for transmitting further comprises data storage means for recording said data received from the sensor means.

19. The wearable apparatus of claim 19, wherein said receiving/sending means further comprises access means for enabling access to information recording in the data storage means from a remote location.

20. The wearable apparatus of claim 1, wherein the means for transmitting further comprises processor means for evaluating values received from the sensor means with respect to acceptable physiological ranges for each value received by the processor means.

21. The wearable apparatus of claim 20, further comprising alarm means for generating a human perceptible signal when the values received from the sensor means are not within acceptable physiological ranges.

22. The wearable apparatus of claim 1, wherein the apparatus further comprises global positioning means for determining the location of the person.

23. The wearable apparatus of claim 22, wherein the apparatus further comprises antenna means for communicating the location of the person to a remote location.

24. The wearable apparatus of claim 23, wherein the antenna means comprises a GPS antenna.

25. The wearable apparatus of claim 22, wherein the apparatus further comprises display means for displaying indicia representing the location of the person.

26. The wearable apparatus of claim 22, wherein the global positioning means is configured to be disposed on the person.

27. A personnel status monitoring system comprising the wearable apparatus of claim 24, and further comprising:
   a portable, remote monitoring unit comprising:
      communications means for receiving data transmitted by the means for transmitting; and
      display means for displaying data representative of the values of the at least one physiological parameter detected by the sensor means, and for displaying indicia representing the geolocation of the person.

28. A personnel status monitoring system of claim 105, wherein the communication means further comprises means for controlling the means for transmitting to control sending of the data supplied by the means responsive to the sensor means.

29. A personnel status monitoring system of claim 27, wherein the remote monitoring unit further comprises a data storage mechanism having a plurality of acceptable ranges for physiological values stored therein, and processor means for comparing the data received from the means responsive to the sensors with the acceptable ranges stored in the data storage mechanism.

30. A personnel status monitoring system of claim 29, wherein the data storage mechanism further comprises means for storing the data received from the means for transmitting.

31. A personnel status monitoring system of claim 29, wherein the portable, remote monitoring unit comprises a portable computer.

32. A personnel status monitoring system of claim 27, wherein the portable, remote monitoring unit comprises a portable unit having a display screen and a data entry means for communicating with the means for transmitting.

33. A personnel status monitoring system of claim 32, wherein the portable, remote monitoring unit is configured to be held in one hand and operated with one hand.

34. A personnel status monitoring system comprising:
   a) support means for wearing by a person on one or more body parts;
   b) sensor means, disposed on the support means, for measuring at least one physiological parameter of the person, and an ambient temperature;
   c) means responsive to the sensor means for transmitting to a remote location, wherein the data indicates values of at least one physiological parameter measured;
   d) global positioning means for determining the position of the person;

e) a portable, remote monitoring unit comprising:
  communications means for receiving data transmitted by the means for transmitting; and
  display means for displaying data representative of values of at least one physiological parameter detected by the sensor means, and for displaying indicia representing the geolocation of the person.

35. The personnel status monitoring system of claim 34, wherein the communications means further comprises means for controlling the means for transmitting to control sending of the data supplied by the means responsive to the sensor means.

36. The personnel status monitoring system of claim 34, wherein the remote monitoring unit further comprises a data storage mechanism having a plurality of acceptable ranges for physiologicalal values stored therein, and processor means for comparing the data received from the means responsive to the sensors with the acceptable ranges stored in the data storage mechanism.

37. The personnel status monitoring system of claim 36, wherein the data storage mechanism further comprises means for storing the data received from the means for transmitting.

38. The personnel status monitoring system of claim 36, wherein the portable, remote monitoring unit comprises a portable computer.

39. The personnel status monitoring system of claim 34, wherein the portable, remote monitoring unit comprises a portable unit having a display screen and a data entry means for communicating with the means for transmitting.

40. The personnel status monitoring system of claim 39, wherein the portable, remote monitoring unit is configured to be held in one hand and operated with one hand.

41. A personnel status monitoring system for monitoring a person, the system comprising:
  a monitoring unit including:
    a) integrated sensor means configured for wearing by a person, the sensor means comprising an oxygen saturation sensor, breathing rate sensor, and blood pressure sensor, a temperature sensor, a heart rate sensor and a motion sensor for generating signals indicative of the person's physiological condition;
    b) processor means disposed in communication with the integrated sensor means for processing signals from the integrated sensor means and for developing data therefrom;
    c) radio communication means disposed in communication with the processor means for conveying the data developed by the processor means to a remote location;
    d) global positioning means for indicating the location of the person wearing the integrated sensor means; and
    d) remote monitoring means for receiving the data conveyed by the radio communications means of the monitoring unit.

42. The personnel status monitoring system of claim 41, wherein the processor means further comprises means configured for controlling an external medical device for delivery of medical treatment to the person when such an external medical device is disposed in communication with the processor means.

43. The personnel status monitoring system of claim 36, wherein the remote monitoring means comprises:
  a mobile leader/medic unit including:
    leader/medic communications means for receiving data from the radio communications means of the monitoring unit; and
    display means for displaying indicia representing data received from the monitoring unit.

44. The personnel status monitoring system of claim 43, wherein the leader/medic communications unit further comprises a data storage means for recording data received from the monitoring unit.

45. The personnel status monitoring system of claim 43, wherein the leader/medic communications unit further comprises a processor means for processing data received from the monitoring unit.

46. The personnel status monitoring system of claim 45, wherein the processor means comprises means for analyzing data received from the monitoring unit and comparing said data to predetermined acceptable physiological ranges.

47. The personnel status monitoring system of claim 46, wherein the leader/medic command unit further comprises means for generating a humanly perceptible alarm signal when the data received from the monitoring unit is not within the acceptable physiological ranges.

48. The personnel status monitoring system of claim 43, wherein the leader/medic unit is configured for one-handed operation.

49. The personnel status monitoring system of claim 44, wherein the remote monitoring means comprises:
  a command unit including:
    central command communications means for receiving data from the radio communications means of the monitoring unit; and
    display means for displaying data received from the monitoring unit.

50. The personnel status monitoring system of claim 49, wherein the command unit further comprises data storage means for recording data received from the monitoring means.

51. The personnel status monitoring system of claim 49, wherein the command unit further comprises processor means for processing data received from the monitoring unit.

52. The personnel status monitoring system of claim 51, wherein the processor means further comprises means for analyzing data received from the monitoring unit and comparing said data to predetermined acceptable physiological ranges.

53. The personnel status monitoring system of claim 49, wherein the system further comprises a leader/medic unit having means for communicating with the monitoring unit, and wherein the command unit comprises means for communicating with the leader/medic unit.

54. The personnel status monitoring system of claim 49, wherein the system further comprises probe means for analyzing a remote area, the problem means comprising:
  a housing;
  a plurality of sensor means disposed within said housing for sensing environmental conditions of the remote area and for generating data indicative of the environmental conditions; and
  communications means for communicating the data to the command unit.

55. The personnel status monitoring system of claim 54, wherein the plurality of sensor means of the probe means comprises at least one sensor for determining the presence of chemical warfare agents.

56. The personnel status monitoring system of claim 54, wherein the plurality of sensor means of the probe means comprises at least one sensor for determining the presence of a biological warfare agent.

57. The personnel status monitoring system of claim 54, wherein the plurality of sensor means of the probe means comprises at least one means for providing optical images.

58. The personnel status monitoring system of claim 54, wherein the plurality of sensor means of the probe means includes at least one microphone.

59. The personnel status monitoring system of claim 54, wherein the plurality of sensor means of the probe means includes at least one sensor selected from the group consisting essentially of an accelerometer, a temperature sensor, an infrared sensor and a motion sensor.

60. The personnel status monitoring system of claim 54, wherein the probe means further comprises a power supply means, and a micro-computer disposed in communication with the sensor means and the power supply means for controlling the plurality of sensor means and for regulating power consumption.

61. A system for monitoring personnel comprising:
at least one soldier unit for wearing by a soldier including:
sensor means having a plurality of sensors for measuring a plurality of physiological parameters and generating signals indicative of the physiological parameters sensed;
a processor means programmed for analyzing the signals and comparing the physiological parameters indicated by the signals to a predetermined range of acceptable physiological parameters;
first wireless communication means for conveying the signals from the sensor means to the processor means;
global positioning means for determining the position of the soldier wearing the soldier unit; and
second wireless communications means disposed in communication with the processor means for conveying signals indicative of the physiological parameters and the position of the soldier to a remote leader/medic unit and/or a remote command unit;
at least one leader/medic unit for use by a leader or medic including:
communications means for receiving signals from the second communications means of the soldier unit indicative of physiological parameters and position of the soldier;
display means for selectively displaying visual indicia representing of the physiological parameters and the position of the soldier; and
input means for selectively controlling whether the display means displays visual indicia representing of physiological parameters or position; and
at least one command unit for communicating with both the at least one soldier unit and the at least one leader/medic unit, the command unit including:
command communication means for communicating with the communication means of the leader/medic unit and the second communications means of the soldier unit;
command processor means disposed in communication with the command communications means for processing signals received from the leader/medic unit and/or the soldier unit, and for providing an alarm signal when one or more of the signals indicates that a physiological parameter monitored by the soldier unit does not fall within the predetermined acceptable range of physiological parameters; and
display means for displaying indicia representing the physiological parameters and/or position of the soldier unit.

62. The system according to claim 61, wherein the sensor means comprises an integrated sensor unit wearable about a soldier's torso, the integrated sensor unit comprising at least one heart rate sensor, at least one temperature sensor, and at least one sensor for monitoring movement of the soldier.

63. The system according to claim 61, wherein the sensor unit comprises a band wearable about the wrist of the soldier, and wherein the sensor means comprises an oxygen saturation sensor and a blood pressure sensor.

64. The system according to claim 63, wherein the soldier unit further comprises controller means configured for operating a medical device.

65. The system according to claim 64, further comprising a medical device disposable in communication with the controller means.

66. The system according to claim 65, wherein the controller means is responsive to the signals indicative of the physiological parameters so as to enable adjustment of the operation of the medical device responsive to changes in the physiological parameters.

67. The system according to claim 61, wherein the soldier unit further comprises display means for displaying indicia representing the position of a soldier unit.

68. The system according to claim 61, wherein the processor means includes medical diagnostic software/firmware for identifying signals indicative of undesirable physiological parameters.

69. The system according to claim 61, wherein the soldier unit further comprises data input means for inputting information into the processor means.

70. The system according to claim 61, wherein the soldier unit further comprises data storage means for recording signals indicative of the physiological parameters.

71. The system according to claim 61, wherein the leader/medic unit further comprises data storage means disposed in communication with the communication means.

72. The system according to claim 61, wherein the leader/medic unit further comprises camera means disposed in communication with the communication means for generating a visual image.

73. The system according to claim 72, wherein the command unit comprises means for displaying visual images generated by the camera means of the leader/medic unit.

74. The system according to claim 61, wherein the command unit further comprises data storage means disposed in communication with the command processor means.

75. The system according to claim 61, wherein the sensor means comprises means for monitoring environmental parameters about the soldier unit.

76. The system according to claim 75, wherein the sensor means comprises a temperature sensor for determining environmental temperature adjacent the soldier unit.

77. The system according to claim 75, wherein the sensor means comprises a humidity sensor for determining environmental humidity.

78. Wearable apparatus for monitoring physiological parameters of a person comprising:
a) support means for wearing by a person on one or more body parts;
b) sensor means, disposed on the support means, for measuring at least one physiological parameter of the person, and an ambient temperature;
c) means responsive to the sensor means for transmitting to a remote location, data indicating values of at least one physiological parameter measured; and
d) a harness having a plurality of pocket means, the means for transmitting being disposed in at least one pocket, and at least one antenna means disposed on the harness and in communication with the means for transmitting.

79. The wearable apparatus of claim 78, wherein the harness comprises a vest, and wherein the means for transmitting is disposed within the vest.

80. The wearable apparatus of claim 78, wherein the apparatus comprises a global positioning means disposed in at least one pocket and in communication with the at least one antenna means.

81. The wearable apparatus of claim 78, further including a strap disposable about the person under the harness, said sensor means being disposed in the strap.

82. The wearable apparatus of claim 81, wherein the apparatus further comprises a wireless network means for conveying data from the sensor means to the means for transmitting.

83. Wearing apparatus for monitoring physiological parameters of a person comprising:

support means for wearing by a person on one or more body parts;

sensor means, disposed on the support means, for measuring multiple physiological parameters of the person including oxygen saturation, breathing rate and blood pressure of the person; and means responsive to the sensor means for transmitting to a remote location data indicating values of each of the multiple physiological parameters measured.

84. Wearable apparatus for monitoring physiological parameters of a person comprising:

(a) support means for wearing by a person on one or more body parts, the support means having a strap mountable about the person's torso;

(b) sensor means, disposed on the support means, for measuring at least one physiological parameter of the person, and an ambient temperature; and (c) means responsive to the sensor means for transmitting to a remote location, data indicating values of at least one physiological parameter measured.

85. The wearable apparatus as in claim 84 wherein the strap includes a plurality of sensors.

86. The wearable apparatus as in claim 84 wherein the sensor means is selected from the group consisting of an accelerometer including filters, an acceleration switch, a heart rate sensor including an ECG sensor, and a body surface temperature sensor.

87. Wearable apparatus for monitoring physiological parameters of a person comprising:

(a) support means for wearing by a person on one or more body parts;

(b) sensor means, disposed on the support means, for measuring a least one physiological parameter of the person, and an ambient temperature;

(c) wherein the sensor means is selected from the group consisting of an accelerometer including filters, an acceleration switch, a heart rate sensor including an ECG sensor, body surface temperature sensor, and an ambient temperature sensor; and (d) means responsive to the sensor means for transmitting to a remote location, data indicating values of at least one physiological parameter measured.

88. The wearable apparatus as in claim 87 wherein the sensor means comprises modular sensor means for selectively changing which physiological parameters are measured.

89. Wearable apparatus for monitoring physiological parameters of a person, comprising:

a) support means for wearing by a person on one or more body parts;

b) sensor means, disposed on the support means, for measuring at least one physiological parameter of the person, and an ambient temperature;

c) a receiving/sending means responsive to the sensor means for transmitting data to and receiving data from a remote location, wherein the data indicates values of at least one physiological parameter measured; and d) a wireless local area network coupled to the receiving sending means for receiving data from the sensor means.

90. The wearable apparatus as in claim 89, wherein the receiving/sending means further comprises data storage means for recording said data received from the sensor means.

91. The wearable apparatus of claim 90, wherein said receiving/sending means further comprises access means for enabling access to information recorded in the data storage means from a remote location.

* * * * *